United States Patent [19]

Houziaux et al.

[11] Patent Number: 5,120,736

[45] Date of Patent: Jun. 9, 1992

[54] 4-METHYL-5-(2-(4-PHENYLPIPERAZIN-1-YL)ETHYL)THIAZOLE DERIVATIVES THEIR METHOD OF PREPARATION AND THE PHARMACEUTICAL COMPOSITIONS IN WHICH THEY ARE PRESENT

[75] Inventors: Patrick Houziaux, Maule; Jean-Pierre Riffaud, Versailles; Jean-Yves LaColle, Saint Nom La Breteche; Bernard Danree, Poissy, all of France

[73] Assignee: Institut de Recherches Chimiques et Biologiques Appliquees, Vicq, France

[21] Appl. No.: 671,719

[22] PCT Filed: Oct. 10, 1989

[86] PCT No.: PCT/FR89/00520

§ 371 Date: Apr. 11, 1991

§ 102(e) Date: Apr. 11, 1991

[87] PCT Pub. No.: WO90/03972

PCT Pub. Date: Apr. 19, 1990

[30] Foreign Application Priority Data

Oct. 11, 1988 [FR] France .................. 88 13375

[51] Int. Cl.$^5$ .................. A61K 31/495; C07D 417/06
[52] U.S. Cl. .................. 54/252; 544/369
[58] Field of Search .................. 544/369; 514/252

[56] References Cited

FOREIGN PATENT DOCUMENTS

| 364350 | 4/1990 | European Pat. Off. | 544/369 |
| 409048 | 1/1991 | European Pat. Off. | 544/369 |
| 2594335 | 8/1987 | France . | |
| 1061247 | 3/1967 | United Kingdom | 544/369 |

OTHER PUBLICATIONS

Chemical Abstracts, vol. 85, No: 11, Sep. 13, 1976, (Columbus, Ohio, US), see p. 550, abstract 78164f.
Chemical Abstracts, vol. 100, No: 19, May 7, 1984, (Columbus, Ohio, US), M. Bogdal et al.: "Thiazole derivatives. IV. Synthesis and pharmacological screening of 2-methyl-5-)2-N-substituted-aminoethyl) thiazoles", see p. 529, abstract 156531t.

*Primary Examiner*—Cecilia Shen

[57] ABSTRACT

The present invention relates to novel 4-methyl-5-[2-(4-phenylpiperazin-1-yl)ethyl]thiazole derivatives of the general formula

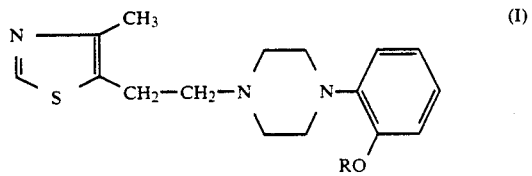

in which R is selected from a hydrogen atom, an alkyl radical having from 2 to 7 carbon atoms and an aralkyl radical of which the aryl moiety preferably consists of phenyl and of which the alkyl moiety has from 1 to 4 carbon atoms, and to the pharmaceutically acceptable salts of these derivatives.

It further relates to a method of preparing these products and to pharmaceutical compositions in which they are incorporated.

These derivatives are applied especially in the preparation of drugs intended for the treatment of functional dysuria associated with hyperactivity of the α-adrenergic sympathetic nervous system.

10 Claims, No Drawings

4-METHYL-5-(2-(4-PHENYLPIPERAZIN-1-YL)ETHYL)THIAZOLE DERIVATIVES THEIR METHOD OF PREPARATION AND THE PHARMACEUTICAL COMPOSITIONS IN WHICH THEY ARE PRESENT

The present invention relates, by way of novel products, to the products of the following general formula:

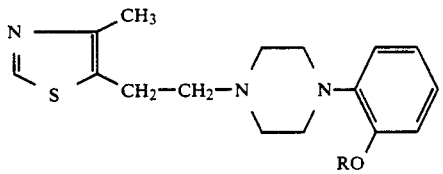

in which R is selected from a hydrogen atom, an alkyl radical having from 2 to 7 carbon atoms and an aralkyl radical of which the aryl moiety preferably consists of phenyl and of which the alkyl moiety has from 1 to 4 carbon atoms, it being possible for said products to take the form of pharmaceutically acceptable salts.

In formula (I), the alkyl or aralkyl radicals can have a linear or branched chain.

An alkyl group having from 2 to 7 carbon atoms is, for example, ethyl, propyl, isopropyl, butyl, tert-butyl, pentyl, neopentyl, isopentyl, hexyl or heptyl.

An aralkyl radical is, for example, benzyl, ethylphenyl, propylphenyl or methylnaphthyl, preferably benzyl.

The salts of the products of formula (I) are obtained in known manner by bringing a product of formula (I) into contact with an appropriate amount of a pharmaceutically acceptable acid such as, for example, a mineral acid like hydrochloric acid or sulfuric acid, or an organic acid like citric, tartaric, maleic or methanesulfonic acid.

4-Methyl-5-[2-(4-phenylpiperazin-1-yl)ethyl]-thiazole is described in French patent application no. 2 594 335.

Derivatives of this compound have also been described in the publications Acta-Pol. Pharm. 40(2), page 159 and Pol. Pl. 78 185, 19 May 1975. However, the products of formula (I) and their salts have never been described in the literature.

The present invention further relates to a method of preparing products of formula (I), said method consisting in reacting, with one equivalent of 4-methyl-5-β-chloroethylthiazole, either two equivalents of 4-phenylpiperazine substituted in the 2-position on the phenyl by a group OR, in which R is as defined above, or one equivalent of 4-picoline and one equivalent of substituted 4-phenylpiperazine, or one equivalent of substituted 4-phenylpiperazine and an excess of anhydrous sodium carbonate, and, if desired, in converting the resulting product to one of its pharmaceutically acceptable salts. Said reaction is generally carried out with heating and in a solvent medium.

The present invention further relates to a pharmaceutical composition containing at least one product of formula (I) as the active product, it being possible for said composition to be useful especially in the field of urology.

According to this feature, the invention also aims to cover a method of preparing drugs useful especially in the field of urology, which comprises incorporating at least one product of formula (I), as the active product, into a pharmaceutically acceptable vehicle, excipient or carrier.

4-Methyl-5-[2-(4-phenylpiperazin-1-yl)ethyl]-thiazole, described in French patent application 2 594 335, is also recommended as an active ingredient in drugs useful in the field of urology.

However, as will be demonstrated below, all the compounds according to the present invention possess very valuable pharmacological properties and, in particular, have a 50% effective dose ($ED_{50}$) which is very appreciably lower than that of this compound known in the prior art.

It has been discovered, unexpectedly, that the particular family of 4-methyl-5-[2-(4-phenylpiperazin-1-yl)ethyl]thiazole derivatives containing a hydroxyl or alkoxy group in the 2-position on the terminal phenyl ring have very valuable pharmacological properties and that the toxicity of these derivatives is sufficiently low to enable them to be used in therapeutics.

The same also applies to the derivative containing a methoxy group in the 2-position on the phenyl ring. This compound is not claimed as a novel product since it has been described in the afore-mentioned publication ACTA Pol. Pharm. 40(2), page 159. However, the known activity of said compound is quite different from the activity demonstrated by the Applicant.

It is for this reason that the invention further relates to the use of the compounds of aforementioned formula (I), in which the radical R is as defined above and can also be a methyl radical, in the preparation of drugs useful for the treatment of functional dysuria associated with hyperactivity of the α-adrenergic sympathetic nervous system.

According to a last feature, the present invention also aims to cover a method of treating functional dysuria associated with hyperactivity of the α-adrenergic sympathetic nervous system, which comprises administering an effective amount of at least one compound of general formula (I), in which the radical R is as defined above and can also be a methyl radical.

The invention will be illustrated in greater detail by the following non-limiting Examples. In these Examples, the $AgNO_3$ assay is a test of product purity.

EXAMPLE 1

Synthesis of 4-methyl-5-[2-(4-o-ethoxyphenylpiperazin-1-yl)ethyl]thiazole trihydrochloride. Code name: B 1211. Product of formula (I) where R=ethyl, in the form of the trihydrochloride.

1) Preparation of 4-methyl-5-[2-(4-o-ethoxyphenyl-piperazin-1-yl)ethyl]thiazole

The following are introduced into a 100 ml three-necked flask equipped with a condenser, a pneumatic stirrer, a thermometer and a dropping funnel:

41.26 g (0.2 mol) of 1-o-ethoxyphenylpiperazine
16.17 g (0.1 mol) of 4-methyl-5-β-chloroethylthiazole The reaction medium is heated at 150° C. for 1 h.

After cooling to room temperature, it is poured into a 5% solution of sodium bicarbonate.

The aqueous phase obtained is extracted with 3×150 ml of methylene chloride.

The combined organic phases are washed with a saturated aqueous solution of sodium chloride and dried over sodium sulfate. After filtration, the solvent is driven off under vacuum.

This gives 31.49 g of crude product (crude yield=95%). This is purified by fractional distillation under vacuum.

22.50 g of a brown liquid are isolated (yield after distillation=67.9%); b.p.$_{0.4\ mm\ Hg}$=185°-190° C.; GC purity>99%.

2) Preparation of the trihydrochloride:

16.57 (0.05 mol) of this product are dissolved in anhydrous ethyl ether.

The solution is saturated with a stream of dry gaseous hydrochloric acid in an ice bath. The crystals formed are filtered off on a glass frit, washed with anhydrous ethyl ether and then dried under vacuum over potassium hydroxide at 70° C.

This gives 19.24 g of beige crystals (crude yield=87.3%).

After recrystallization from a 1/3 isopropanol/ethanol mixture, 16.0 g of white crystals are isolated (yield after recrystallization=72.6%).

Said crystals have a melting point m.p.$_{KB}$ of 212°-213° C., IR and NMR spectra consistent with the proposed structure, a GC purity of >99% and an AgNO$_3$ titer of 100.2%.

EXAMPLE 2

Synthesis of 4-methyl-5-[2-(4-o-hydroxyphenylpiperazin-1-yl)ethyl]thiazole dihydrochloride. Code name: B 1302. Product of formula (I) where R=hydrogen, in the form of the dihydrochloride.

1) Preparation of 4-methyl-5-[2-(4-o-hydroxyphenyl-piperazin-1-yl)ethyl]thiazole The following are introduced into a 100 ml three-necked flask equipped with a condenser, a pneumatic stirrer, a thermometer and a dropping funnel:

35.65 g (0.2 mol) of 1-o-hydroxyphenylpiperazine 16.17 g (0.1 mol) of 4-methyl-5-β-chloroethylthiazole The reaction medium is heated at 150° C. for 1 h.

After cooling to room temperature and the addition of methylene chloride, it is poured into a saturated aqueous solution of sodium chloride.

The organic phase is decanted and the aqueous phase is extracted with 2×150 ml of methylene chloride.

The combined organic phases are washed with a saturated aqueous solution of sodium chloride and dried over sodium sulfate. After filtration, the solvent is driven off under vacuum.

This gives 27.61 g of a brown oil (crude yield=91%) having a GC purity of 97%.

2) Preparation of the dihydrochloride:

15 17 g (0.05 mol) of this crude product are dissolved in 430 ml of anhydrous ethyl ether.

The solution is saturated with a stream of dry gaseous hydrochloric acid in an ice bath.

The crystals formed are filtered off on a glass frit, washed with anhydrous ethyl ether and then dried under vacuum over potassium hydroxide at 70° C.

This gives 18.06 g of beige crystals (crude yield=96%).

After two recrystallizations from a 1/1 isopropanol/methanol mixture, 4.80 g of light beige crystals are isolated (yield after recrystallizations=25.5%).

Said crystals have a melting point m.p.$_{KB}$ of 250°-255° C., IR and NMR spectra consistent with the proposed structure and an AgNO$_3$ titer of 100.5%.

EXAMPLE 3

Synthesis of 4-methyl-5-[2-(4-o-butoxyphenylpiperazin-1-yl)ethyl]thiazole monohydrochloride. Code name: B 1341. Product of formula (I) where R=butyl, in the form of the monhydrochloride 1) Preparation of 4-methyl-5-[2-(4-o-butoxyphenyl-piperazin-1-yl)ethyl]thiazole The following are introduced into a 100 ml three-necked flask equipped with a condenser, a pneumatic stirrer, a thermometer and a dropping funnel:

46.87 g (0.2 mol) of 1-o-butoxyphenylpiperazine 16.17 g (0.1 mol) of 4-methyl-5-β-chloroethylthiazole The reaction medium is heated at 150° C. for 1 h.

After cooling to room temperature and the addition of ethyl ether, it is poured into H$_2$O. The organic phase is decanted and the remaining aqueous phase is extracted with twice 150 ml of ethyl ether. The combined organic phases are washed with a saturated aqueous solution of sodium chloride and dried over sodium sulfate. After filtration, the solvent is driven off under vacuum.

This gives 33.76 g of a brown oil (crude yield=93.9%), which is purified by fractional distillation under vacuum.

24.16 g of an orange liquid are isolated (yield after distillation=67.2%); b.p.$_{0.1\ mm\ Hg}$=180°-185° C.; GC purity=98.8%.

2) Preparation of the monohydrochloride:

17.97 g (0.05 mol) of this product are dissolved in absolute ethanol.

After cooling in an ice bath, 43.5 ml of an ethanolic solution of HCl (containing 1.15 mol of HCl per liter) are added.

After stirring for 30 min, the mixture is concentrated to dryness under vacuum and the residue is taken up with anhydrous ether.

The crystals formed are filtered off on a glass frit, washed with anhydrous ethyl ether and then dried under vacuum over potassium hydroxide at 70° C.

This gives 19.16 of beige crystals (crude yield=96.8%).

After recrystallization from isopropanol, 16.06 g of white crystals are isolated (yield after recrystallization=81.1%).

Said crystals have a melting point m.p.$_{KB}$ of 180°-185° C., IR and NMR spectra consistent with the proposed structure, an AgNO$_3$ titer of 98.6% and a GC purity of >99.5%.

EXAMPLE 4

Synthesis of 4-methyl-5-[2-(4-o-pentoxyphenylpiperazin-1-yl)ethyl]thiazole monohydrochloride. Code name: B 1357. Product of formula (I) where R=pentyl, in the form of the monohydrochloride.

1) Preparation of 4-methyl-5-[2-(4-o-pentoxyphenyl-piperazin-1-yl)ethyl]thiazole The following are introduced into a 100 ml three-necked flask equipped with a condenser, a pneumatic stirrer and a thermometer:

27.32 g (0.11 mol) of 1-o-pentoxyphenylpiperazine 8.89 g (0.055 mol) of 4-methyl-5-β-chloroethyl-thiazole The reaction medium is heated at 150° C. for 1 h 30 min.

After cooling to room temperature and the addition of 200 ml of ethyl ether, it is poured into 200 ml of H$_2$O. The organic phase is decanted and the remaining aqueous phase is extracted with twice 100 ml of ethyl ether. The combined organic phases are washed with a saturated aqueous solution of sodium chloride and dried over sodium sulfate. After filtration, the solvent is driven off under vacuum.

This gives 19.04 g of a brown oil (crude yield=92.6%), which is purified by fractional distillation under vacuum.

13.25 g of an orange liquid are isolated (yield after distillation=64.5%).

B.p.$_{0.1\ mm\ Hg}$=190°-193° C.; GC purity=99.9%; perchloric titer=100.6%.

2) Preparation of the monohydrochloride 12.44 g (0.0333 mol) of this product are dissolved in 150 ml of absolute ethanol. The solution is cooled in an ice bath and 23.1 ml of an ethanolic solution of HCl (containing 1.44 mol of HCl per liter) are added.

After stirring for 5 min, the mixture is concentrated to dryness under vacuum and the residue is taken up with anhydrous ethyl ether.

The crystals formed are filtered off on a glass frit, washed with ethyl ether and then dried under vacuum over potassium hydroxide at 70° C.

This gives 13.38 g of beige crystals (crude yield: 98%).

After recrystallization from an ethyl acetate/isopropanol mixture (20/1), 10.35 g of white crystals are isolated (yield after recrystallization=75.8%).

Said crystals have a melting point m.p.$_{KB}$ of 156°-158° C., IR and NMR spectra consistent with the proposed structure, an AgNO$_3$ titer of 97.7% and a GC purity of 99.9%.

EXAMPLE 5

Synthesis of 4-methyl-5-[2-(4-o-isopropoxyphenyl-piperazin-1-yl)ethyl]thiazole monohydrochloride. Code name: B 1398. Product of formula (I) where R=isopropyl, in the form of the monohydrochloride.

1) Preparation of 4-methyl-5-[2-(4-o-isopropoxy-phenylpiperazin-1-yl)ethyl]thiazole The following are introduced into a 100 ml three-necked flask equipped with a condenser, a pneumatic stirrer and a thermometer:

29.41 g (0.133 mol) of 1-o-isopropoxyphenylpiperazine 10 g (0.062 mol) of 4-methyl-5-β-chloroethylthiazole The reaction medium is heated at 150° C. for 1 h.

After cooling to room temperature and the addition of methylene chloride, it is poured into a 10% solution of NaHCO$_3$. The organic phase is decanted and the remaining aqueous phase is extracted with twice 100 ml of CH$_2$Cl$_2$. The combined organic phases are washed with a saturated aqueous solution of sodium chloride until the washings are neutral, and dried over sodium sulfate. After filtration, the solvent is driven off under vacuum.

This gives a crude oil containing the excess of 1-o-isopropoxyphenylpiperazine which has served as an HCl acceptor. Purification is effected by fractional distillation under vacuum.

17.2 g of an orange liquid are isolated (yield after distillation=80.5%).

B.p.$_{0.15\ mm\ Hg}$=225°-230° C.; GC purity=99%.

2) Preparation of the monohydrochloride 17.2 g (0.05 mol) of this product are dissolved in 60 absolute ethanol.

After cooling in an ice bath, 37 ml of an ethanolic solution of HCl (containing 1.35 mol of HCl per liter) are added.

After stirring for 5 min, the precipitate thus formed is filtered off on a glass frit, washed with anhydrous ethyl ether and then dried under vacuum over potassium hydroxide at 70° C.

This gives 13.9 g of white crystals (crude yield: 72.7%).

After recrystallization from an ethyl acetate/ethanol mixture (3/1), 11.6 g of white crystals are isolated (yield after recrystallization: 60.6%).

Said crystals have a melting point m.p.$_{KB}$ of 196°-200° C., IR and NMR spectra consistent with the proposed structure, an AgNO$_3$ titer of 98% and a GC purity of 99.9%.

EXAMPLE 6

Synthesis of 4-methyl-5-[2-(4-o-methoxyphenylpiper-azin-1-yl)ethyl]thiazole trihydrochloride. Code name: B 1433. Product of formula (I) where R=methyl.

1) Preparation of 4-methyl-5-[2-(4-o-methoxyphenyl-piperazin-1-yl)ethyl]thiazole The following are introduced into a 500 ml three-necked flask equipped with a condenser, a pneumatic stirrer, a thermometer and a dropping funnel:

210 ml of butan-1-ol 10.66 (0.0554 mol) of 1-o-methoxyphenylpiperazine in portions, 8.81 g (0.0831 mol) of anhydrous Na$_2$CO$_3$.

8.96 (0.0554 mol) of 4-methyl-5-β-chloroethyl-thiazole are added dropwise.

The reaction medium is refluxed for 50 h.

After hot filtration of the reaction medium and washing of the insoluble salts with ethanol, the filtrate is concentrated to dryness under vacuum.

This gives 15.2 g of a brown oil (crude yield: 86.4%) having a GC purity of 94.2%.

2) Preparation of the trihydrochloride 14.5 g (0.0457 mol) of this product are dissolved in 80 ml of anhydrous ethyl ether.

After cooling in an ice bath, the solution is saturated with gaseous HCl by bubbling.

The mixture is stirred for 15 min. The crystals formed are filtered off on a glass frit, washed with anhydrous ethyl ether and then dried under vacuum over potassium hydroxide at 70° C.

This gives 17.06 g of crystals (crude yield: 87.5%).

After recrystallization from 330 ml of ethanol, 9 g of white crystals are isolated (yield after recrystallization=46.2%).

Said crystals have a melting point m.p.$_{KB}$ of 210°-212° C., IR and NMR spectra consistent with the proposed structure, an AgNO$_3$ titer of 96.5% and a GC purity of 99.9%.

EXAMPLES 7 TO 11

Experimental procedures similar to those just described, which those skilled in the art will easily be able to work out, were used to prepare the compounds of formula (I) in which R is respectively a propyl radical (Example 7), an isobutyl radical (Example 8), an isopentyl radical (Example 9), a neopentyl radical (Example 10) and a benzyl radical (Example 11).

The formulae and the physical properties of the products synthesized in Examples 1 to 11 have been collated in Summary Table no. 1.

The toxicity and the pharmacological properties of the products of formula I were tested; the results obtained are described below.

1) Acute toxicity in mice:

Principle of the measurement

The products were administered orally, in a single dose, to male mice with an average weight of 22 g. The mortality was recorded after an observation period of 14 days.

The results are expressed in the form of the 50% lethal dose ($LD_{50}$), i.e. the theoretical dose in $mg.kg^{-1}$, administered orally, which causes the death of 50% of the animals.

Results

These are reported in Table 2.

Virtually all the molecules have an $LD_{50}$ of more than $1 g.kg^{-1}$. These products therefore have a low toxicity after a single administration.

2) Determination of the alpha-blocking activity on isolated rat vas deferens a) Principle of the measurement Stimulation of the post-synaptic alpha-adrenergic receptors by norepinephrine causes contraction of the isolated vas deferens.

The concentration of product in whose presence the norepinephrine concentration must be doubled to obtain the same effect as in the absence of said product is determined.

The logarithm of this concentration, with its sign changed, constitutes the $pA_2$ of the products.

b) Results obtained

The $pA_2$ values reported in Table 3 show that the products behave as competitive norepinephrine antagonists at the alpha-adrenergic receptors.

Their alpha-blocking activity is high since it appears for low concentrations of between $2.10^{-7}$ M and $10^{-8}$ M.

3) Determination of the adrenolytic activity "in vivo" in rats:

a) Principle of the measurement

The intravenous injection of norepinephrine (0.4 $mg.kg^{-1}$) into wake rats causes the death of 100% of the animals. The prior administration of a substance with an alpha-blocking property enables this toxicity to be reduced.

The results are expressed in the form of the 50% effective dose ($ED_{50}$), i.e. the dose in $mg.kg^{-1}$ which protects 50% of the animals.

b) Results obtained

The $ED_{50}$ values corresponding to the products of Examples 1 to 11 are shown in Table 4.

The majority of the products are active at relatively low doses. Their adrenolytic activity in the whole animal is therefore very high, thus confirming the effects demonstrated in vitro.

It should be noted that the $ED_{50}$ of all these compounds is very considerably lower (a gain of about 40% to about 90%) than that of 4-methyl-5-[2-(4-phenylpiperazin-1-yl)ethyl]thiazole (which is 8.7 $mg.kg^{-1}$ under the same conditions).

These results show the value of these compounds and their distinct superiority over the most similar compound of the state of the art.

4) Determination of the inhibitory action of the compounds towards the increase in ureteral pressure induced in rabbits by the intravenous administration of norepinephrine a) Principle of the measurement The ureteral pressure is measured by catheterization of the prostatic ureter of anesthetized male rabbits. The increase in ureteral pressure is induced by an intravenous injection of norepinephrine. This hyperpressure can be inhibited by the prior administration of molecules with alpha-blocking potential.

B 1211, B 1302, B 1341, B 1357, B 1398 and B 1433 were the only compounds to be tested on this model.

b) Results obtained

These are shown in Table 5 in the form of the 50% inhibitory dose ($ID_{50}$), which is defined as being the dose of product which, when administered intravenously, causes a 50% inhibition of the ureteral hyperpressure induced by norepinephrine.

The compounds tested are particularly effective with active doses of less than $1 mg.kg^{-1}$.

B 1398 is remarkably effective.

These data make it possible to predict a good therapeutic activity for these molecules in functional dysuria associated with hyperactivity of the alpha-adrenergic sympathetic nervous system.

The products can be administered by a general route (parenterally, orally, rectally) or topically.

The pharmaceutical compositions in which at least one product according to the invention is present as the active ingredient, in combination with a pharmaceutically acceptable vehicle, can be solid or liquid and can take the form of, for example, injectable preparations, tablets, gelatin capsules or granules. The dosage can vary within wide limits, depending in particular on the type and severity of the complaint to be treated and on the mode of administration.

Most frequently, the adult dosage is between 0.05 and 0.5 g per day by parenteral administration and between 0.1 and 4 g per day by oral administration.

TABLE 1

GENERAL FORMULA:

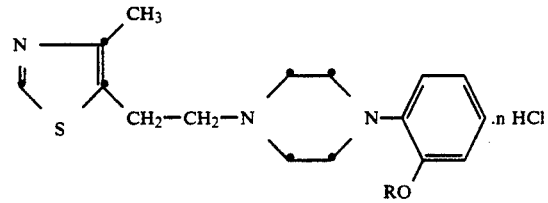

| Example | R | n | B code | Empirical formula | MW | M.p.$_{KB}$ (°C.) |
|---|---|---|---|---|---|---|
| 1 | —$C_2H_5$ | 3 | 1211 | $C_{18}H_{28}Cl_3N_3OS$ | 440.85 | 212–213 |
| 2 | —H | 2 | 1302 | $C_{16}H_{23}Cl_2N_3OS$ | 376.35 | 250–255 |
| 3 | —$(CH_2)_3$—$CH_3$ | 1 | 1341 | $C_{20}H_{30}ClN_3OS$ | 396.0 | 180–185 |
| 4 | —$(CH_2)_4$—$CH_3$ | 1 | 1357 | $C_{21}H_{32}ClN_3OS$ | 410.04 | 156–158 |
| 7 | —$(CH_2)_2$—$CH_3$ | 1 | 1359 | $C_{19}H_{28}ClN_3OS$ | 381.96 | 189–190 |

TABLE 1-continued

GENERAL FORMULA:

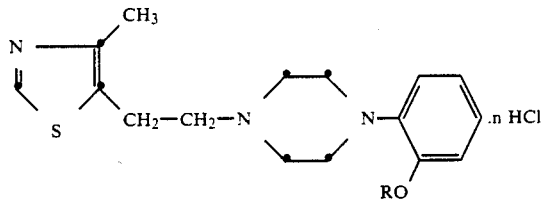

| Example | R | n | B code | Empirical formula | MW | M.p.$_{KB}$ (°C.) |
|---|---|---|---|---|---|---|
| 5 | —CH(CH₃)₂ | 1 | 1398 | C₁₉H₂₈ClN₃OS | 381.96 | 196-200 |
| 8 | —CH₂—CH(CH₃)₂ | 1 | 1422 | C₂₀H₃₀ClN₃OS | 395.95 | 188-189 |
| 9 | —(CH₂)₂—CH(CH₃)₂ | 1 | 1423 | C₂₁H₃₂ClN₃OS | 410.04 | 160-162 |
| 10 | —CH₂—C(CH₃)₃ | 1 | 1424 | C₂₁H₃₂ClN₃OS | 410.04 | 200-202 |
| 11 | —CH₂—C₆H₅ | 2 | 1425 | C₂₃H₂₉Cl₂N₃OS | 466.45 | 175-180 |
| 6 | —CH₃ | 3 | 1433 | C₁₇H₂₆Cl₃N₃OS | 426.82 | 210-212 |

TABLE 2

ACUTE TOXICITY OF THE COMPOUNDS IN MICE AFTER A SINGLE ORAL ADMINISTRATION (LD$_{50}$ = 50 percent lethal dose)

| | B code | | | | | | | | | | |
|---|---|---|---|---|---|---|---|---|---|---|---|
| | 1211 | 1302 | 1341 | 1357 | 1359 | 1398 | 1422 | 1423 | 1424 | 1425 | 1433 |
| LD$_{50}$ mg · kg$^{-1}$ p.o. | >1000 | 490 | >1000 | >1000 | >1000 | >1000 | >1000 | >1000 | >1000 | >1000 | >1000 |

TABLE 3

ALPHA-BLOCKING ACTIVITY OF THE COMPOUNDS TOWARDS NOREPINEPHRINE ON ISOLATED RAT VAS DEFERENS

| | B code | | | | | | | | | | |
|---|---|---|---|---|---|---|---|---|---|---|---|
| | 1211 | 1302 | 1341 | 1357 | 1359 | 1398 | 1422 | 1423 | 1424 | 1425 | 1433 |
| pA$_2$ | 7.58 | 6.90 | 8.0 | 7.77 | 7.24 | 7.77 | 7.44 | 7.34 | 6.7 | 7.20 | 7.84 |

TABLE 4

ADRENOLYTIC ACTIVITY OF THE COMPOUNDS TOWARDS THE LETHAL EFFECT OF NOREPINEPHRINE IN RATS BY ORAL ADMINISTRATION (ED$_{50}$ = 50 percent effective dose)

| | B code | | | | | | | | | | |
|---|---|---|---|---|---|---|---|---|---|---|---|
| | 1211 | 1302 | 1341 | 1357 | 1359 | 1398 | 1422 | 1423 | 1424 | 1425 | 1433 |
| ED$_{50}$ mg · kg$^{-1}$ p.o. | 2 | 4 | 1 | 1.80 | 1.93 | 0.44 | 1.60 | 2.35 | 2.04 | 5 | 2.66 |

TABLE 5

INHIBITORY ACTION OF THE COMPOUNDS ON THE INCREASE IN
URETERAL PRESSURE INDUCED IN RABBITS BY THE INTRAVENOUS
ADMINISTRATION OF NOREPINEPHRINE
($ID_{50}$: 50 percent inhibitory dose)

| | B code | | | | | | | | | | |
|---|---|---|---|---|---|---|---|---|---|---|---|
| | 1211 | 1302 | 1341 | 1357 | 1359 | 1398 | 1422 | 1423 | 1424 | 1425 | 1433 |
| $ID_{50}$ mg · kg$^{-1}$ i.v. | 0.16 | 0.44 | 0.39 | 0.46 | — | 0.09 | — | — | — | — | 0.3 |

What is claimed is:

1. A 4-methyl-5-thiazole compound of the formula

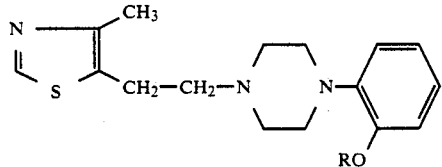
(I)

in which R is selected from the group consisting of a hydrogen atom, an alkyl radical having from 2 to 7 carbon atoms and an aralkyl radical of which the aryl moiety consists of phenyl or naphthyl, or optionally lower alkyl substituted phenyl or naphthyl and of which the alkyl moiety has from 1 to 4 carbon atoms, or a pharmaceutically acceptable salt thereof.

2. A compound according to claim 1, wherein R is selected from the group consisting of a hydrogen atoms, a methyl radical, an ethyl radical, an isopropyl radical, a butyl radical and a pentyl radical.

3. A pharmaceutical composition for the treatment of functional dysuria associated with hyperactivity of the -adrenergic sympathetic nervous system, said composition containing an effective amount of at least one compound according to claim 8 as the active ingredient, in combination with a pharmaceutically acceptable vehicle, excipient or carrier.

4. A pharmaceutical composition for the treatment of functional dysuria associated with hyperactivity of the -adrenergic sympathetic nervous system, said composition containing an effective amount of at least one compound according to claim 2 as the active ingredient, in combination with a pharmaceutically acceptable vehicle, excipient or carrier.

5. A 4-methyl-5-thiazole compound of the formula

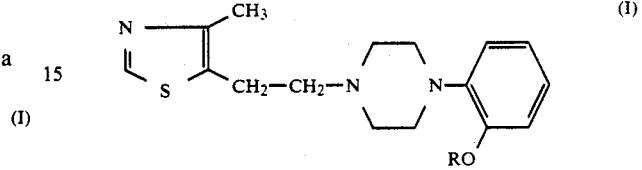
(I)

in which R is selected from the group consisting of a hydrogen atom, an alkyl radical having from 2 to 7 carbon atoms, an aralkyl radical or a pharmaceutically acceptable salt thereof.

6. A compound according to claim 5, wherein R is selected from the group consisting of a hydrogen atom, an ethyl, an isopropyl, a butyl and a pentyl radical.

7. A pharmaceutical composition for the treatment of functional dysuria associated with hyperactivity of the -adrenergic sympathetic nervous system, said composition containing an effective amount of at least one compound according to claim 5 as the active ingredient, in combination with a pharmaceutically acceptable vehicle, excipient or carrier.

8. A method of treating functional dysuria associated with hyperactivity of the -adrenergic sympathetic nervous system, which comprises administering an effective amount of at least one compound according to claim 1, or a pharmaceutically acceptable salt thereof.

9. A method of treating functional dysuria associated with hyperactivity of the -adrenergic sympathetic nervous system, which comprises administering an effective amount of at least one compound according to claim 5, or a pharmaceutically acceptable salt thereof.

10. A method of treating functional dysuria associated with hyperactivity of the -adrenergic sympathetic nervous system, which comprises administering an effective amount of 4-methyl-5-thiazole or a pharmaceutically acceptable salt thereof.

* * * * *